United States Patent [19]

Mönch

[11] Patent Number: 4,732,187
[45] Date of Patent: Mar. 22, 1988

[54] DEVICE FOR DISINFECTING MEDICAL INSTRUMENTS

[76] Inventor: Harry Mönch, Schwabstrasse 4, 7134 Knittlingen, Fed. Rep. of Germany

[21] Appl. No.: 793,542

[22] Filed: Oct. 31, 1985

[51] Int. Cl.$^4$ .............................................. B08B 3/04
[52] U.S. Cl. ................................. 134/135; 134/113; 422/297; 422/300
[58] Field of Search ............ 422/300, 292, 297; 134/84, 104, 113, 135, 182; 206/363, 364, 365, 366, 367, 368, 369, 370, 212, 499; 99/410, 412, 413, 414, 415; 126/369

[56] References Cited

U.S. PATENT DOCUMENTS

| | | | |
|---|---|---|---|
| 1,187,498 | 6/1916 | Castle | 422/300 |
| 1,538,571 | 5/1925 | Meinecke et al. | 422/300 |
| 1,939,715 | 12/1933 | Meitzler | 422/300 |
| 3,331,309 | 7/1967 | Proffitt | 99/411 |
| 3,534,677 | 10/1970 | Keathley | 99/411 |
| 3,714,889 | 2/1973 | Mazzola et al. | 99/411 |
| 3,966,408 | 6/1976 | Drennen et al. | 134/135 X |
| 4,053,280 | 10/1977 | Salisbury | 134/135 X |
| 4,146,404 | 3/1979 | Williams, Jr. | 134/135 X |
| 4,458,705 | 7/1984 | Cawood | 422/300 X |
| 4,582,076 | 4/1986 | Prat | 134/113 X |

Primary Examiner—Harvey C. Hornsby
Assistant Examiner—Frankie L. Stinson
Attorney, Agent, or Firm—Hill, Van Santen, Steadman & Simpson

[57] ABSTRACT

A device for disinfecting medical instruments such as endoscopes and accessories comprises a tub containing disinfectant fluid into which may be dipped a perforated basket with endoscopes and accessories placed therein, which may after the disinfecting action be lifted out of the disinfectant fluid, and after longitudinal displacement relative to the tub may be supported by means of lateral projections for the draining off of residual disinfectant fluid.

6 Claims, 4 Drawing Figures

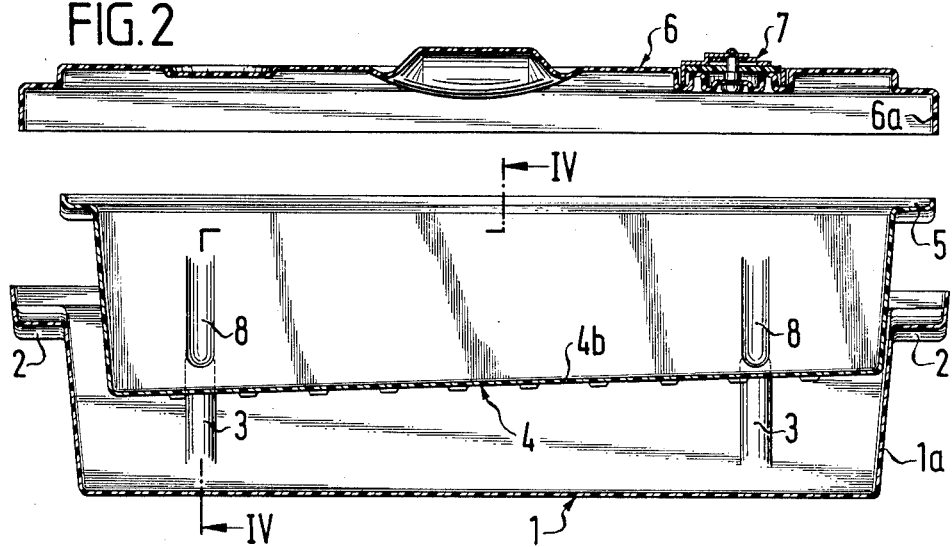
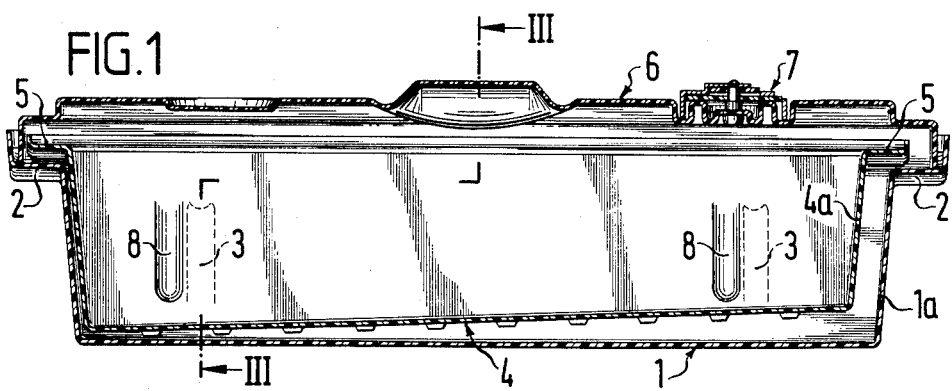
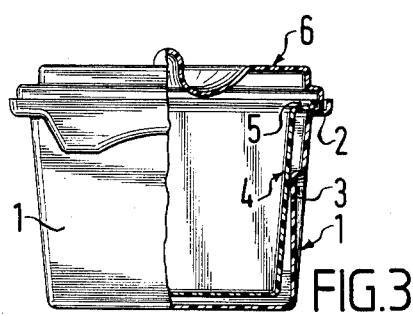
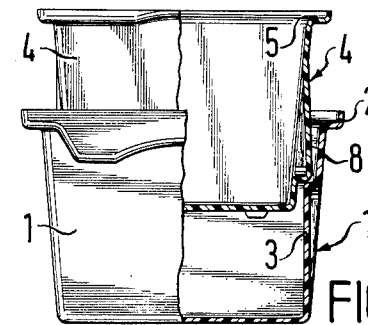

DEVICE FOR DISINFECTING MEDICAL INSTRUMENTS

BACKGROUND OF THE INVENTION

The invention relates to a device for disinfecting medical instruments such as endoscopes and accessories comprising a perforated basket for reception of the endoscopes and accessories and for dipping into a tub containing a disinfectant fluid and closable by a lid.

DESCRIPTION OF THE PRIOR ART

Endoscopes and accessories must be thoroughly disinfected or sterilised prior to being used. Until now, this is performed in such a manner that the instruments placed in a perforated basket are dipped into a tub containing disinfectant fluid and are lifted out with the basket after disinfection. In this connection, it is necessary that the extracted perforated basket containing the instruments must be held above the tub by hand until the disinfectant fluid has drained completely off the basket and the instruments. The personnel is not available for other activities during this time, and it may happen moreover that the draining period required is not adhered to upon holding the basket still by hand, so that the endoscope is placed too early in a bath neutralising the disinfectant fluid. Under particular circumstances, this may necessitate premature replacement of the neutralising fluid, or adequate neutralisation of the residual disinfectant drops may not be obtained, which may lead to trouble for the patient. Since the instruments are placed approximately horizontally in the disinfectant fluid container, an incomplete disinfecting action could be possible moreover, owing to complete wetting of the instrument surfaces and inner wall surfaces because of adhering gas bubbles. It has also been unavoidable until now that the instruments together with the perforated basket are laid temporarily on a contaminated surface, e.g. for draining or repositioning of the instruments, which could lead to a renewed entrainment of germs.

SUMMARY OF THE INVENTION

It is an object of the invention to provide a disinfecting device which allows personnel to be kept free for other activities after the disinfecting operation and during the draining period of the perforated basket containing the instruments, while accomplishing a complete disinfecting operation without appreciable quantities of disinfectant fluid being left behind on or within the instrument after the disinfecting operation.

According to the invention, this object is achieved in that the sidewalls of the perforated basket are provided with projections which in a longitudinally directed position of the basket with respect to the tub after being lifted out of the disinfectant fluid, rest on inner projections of the tub sidewalls to form support means for holding the basket above the fluid for draining. At least three pairs of projections are needed to give the required stability. The immersed perforated basket containing the instruments may after performing the disinfecting operation be lifted out of the disinfectant fluid and supported in the tub, so that it is possible to adhere to the minimum period needed for draining of the disinfectant fluid off the perforated basket and instruments, without an operative having the perform a task, and so that following the draining operation, a total neutralisation of the disinfectant fluid residues may then be performed in any case, without the need for premature replacement of this fluid.

The tub and the basket are preferably substantially rectangular in plan view, with two of said projections on each longitudinal side. Other configurations can however be contemplated, for example a projection on one end wall and a projection on each sidewall near the opposite end.

The invention is described in the following with other advantageous features, with reference to the drawings.

BRIEF DESCRIPTION OF THE DRAWINGS

FIG. 1 shows the disinfecting device comprising a tub, a perforated basket and a lid, in vertical longitudinal cross-section, FIG. 2 shows the same longitudinal cross-section, but with the perforated basket lifted and the lid raised, FIG. 3 shows a cross-section along the broken line III—III of FIG. 1, FIG. 4 shows a cross-section along the broken line IV—IV of FIG. 2.

DETAILED DESCRIPTION OF THE PREFERRED EMBODIMENTS

A device for disinfecting instruments and accessories comprises a rectangular tub 1 having an upper peripheral flange 2 forming a groove, which may comprise handle excisions or recesses. The two sidewalls of the tub each provided close to their extremities with inwardly directed projections 3 which are advantageously notched at their upper extremity.

A perforated basket 4 receiving an endoscope and accessories is placed in this tub which is filled with a disinfectant fluid up to a particular level, and dipped into the disinfectant fluid. Upon being placed in the tub 1, the perforated basket rests with a peripheral flange 5 forming a draining groove on a peripheral flange 2 of the tub 1 equally forming a draining groove. Any disinfecting fluid which may spill over during carrying runs back into the tub through the grooves 2 and 5. This is then followed by closure by putting on a lid 6 provided with a peripheral rim 6a, which is provided with a central handle and embossments, one embossment receiving a device 7, e.g. consisting of discs rotatable with respect to each other, whereby it is possible to record periods, e.g. of days, weeks and months.

Once the period required for disinfection has elapsed, the perforated basket 4 containing the instruments is lifted out of the tub 1 above the level of disinfectant fluid, and is then supported after a relative longitudinal displacement with outer lateral projections 8 on the projections 3 of the inner sidewalls of the tub. To this end, the lower extremities of the projections 8 engage in the notches of the projections 3, and the perforated basket 4 is thereby secured against longitudinal displacements in the raised position. In this relative position of the perforated basket 4 with respect to the tub 1, the end surface 4a of the perforated basket bears against the facing end surface 1a of the tub. The possibility of relative displacement of the basket 4 should to this end be at least equal to the width of the projections 3 and 8.

The perforated basket 4 remains in the lifted position until substantially all of the disinfectant fluid has drained off the instruments and the basket into the tub 1 below. This period may be indicated by means of the device 7.

To accelerate the draining of the disinfectant fluid off the perforated basket and the instruments, it is advantageous to allow the base 4b of the perforated basket to extend slopingly with respect to the horizontal from one end of the basket to the other so that disinfectant fluid may thereby drip off downwards by faster draining off the instruments and the perforated basket.

I claim:

1. A device for disinfecting medical instruments comprising: a tub with a rectangular bottom, a pair of longitudinal sidewalls and a pair of end walls shorter than the sidewalls, said tub receiving a disinfecting fluid and having a perpheral flange with an upwardly extending edge; a perforated basket having a rectangular bottom, a pair of longitudinal sidewalls and a pair of end walls shorter than the sidewalls said basket having a peripheral flange with an upturned edge, said basket being dimensioned to fit within said tub and to receive said instruments therein; a lid having a peripheral rim; and means for supporting the perforated basket in said tub above a fluid level therein, said means for supporting comprising at least four coacting pairs of projections with each pair including an inwardly directed projection on an inner surface of the sidewall of said tub and an external projection on an outer surface of the sidewall of the basket, said tub having an internal length greater than the external length of said basket by at least the width of said projection, said basket being movable in said tub from a first position with one end wall of the basket engaging one end wall of the tub and the projections of each pair being aligned and arranged with each other to hold the basket above a fluid level in the tub to allow the instruments to be drained and a second position with the other end wall of the basket engaging the opposite end wall of the tub and the projections of each pair being out of alignment and engagement with each other to allow the basket with the instruments to be immersed in the fluid of the tub with the flange of the basket resting on the flange of the tub, said lid closing said tub with the rim received on the flange of the tub and surrounding the upturned edge of the flange of the basket.

2. A device as claimed in claim 1, wherein said perforated basket has a base sloping from one end to the other when the top of the basket is horizontal.

3. A device as claimed in claim 1, wherein the lid is provided with a device for setting up time data.

4. A device according to claim 1, wherein one projection of each pair has a notch for receiving the coacting projection, said notch providing stability against lateral movement from said first position.

5. A device according to claim 4, wherein the one projection of each pair is the inwardly directed projection of the tub.

6. A device according to claim 4, wherein said perforated basket has a base sloping from one end to the other when the top of the basket is horizontal.

* * * * *